United States Patent
Hermle et al.

(10) Patent No.: US 9,656,302 B2
(45) Date of Patent: May 23, 2017

(54) DEVICE AND METHOD FOR TRANSPORTING AND EXAMINING FAST-MOVING OBJECTS TO BE TREATED

(71) Applicant: FINATEC HOLDING AG, Brugg bei Biel (CH)

(72) Inventors: Matthias Hermle, Brugg bei Biel (CH); Bernhard Kubalek, Moosseedorf (CH); Fridolin Maibach, Nidau (CH)

(73) Assignee: FINATEC HOLDING AG, Brugg Bei Biel (CH)

( * ) Notice: Subject to any disclaimer, the term of this patent is extended or adjusted under 35 U.S.C. 154(b) by 0 days.

(21) Appl. No.: 14/770,172

(22) PCT Filed: Mar. 14, 2014

(86) PCT No.: PCT/EP2014/055108
§ 371 (c)(1),
(2) Date: Aug. 25, 2015

(87) PCT Pub. No.: WO2014/140280
PCT Pub. Date: Sep. 18, 2014

(65) Prior Publication Data
US 2016/0001328 A1  Jan. 7, 2016

(30) Foreign Application Priority Data
Mar. 14, 2013  (DE) .................. 10 2013 102 653

(51) Int. Cl.
B07C 5/00 (2006.01)
B07C 5/342 (2006.01)
B07C 5/36 (2006.01)
B07C 5/34 (2006.01)
G01N 21/90 (2006.01)

(52) U.S. Cl.
CPC .............. B07C 5/3422 (2013.01); B07C 5/34 (2013.01); B07C 5/363 (2013.01); G01N 21/909 (2013.01)

(58) Field of Classification Search
CPC B07C 5/00; B07C 5/34; B07C 5/3422; B07C 5/363
USPC .......................... 209/577, 639, 644
See application file for complete search history.

(56) References Cited

U.S. PATENT DOCUMENTS

| | | | | |
|---|---|---|---|---|
| 4,581,632 A | * | 4/1986 | Davis ..................... | G01N 21/88 250/223 R |
| 5,366,096 A | * | 11/1994 | Miller .................. | A24C 5/3412 209/535 |
| 5,462,176 A | * | 10/1995 | Hereford .............. | B07C 5/3425 131/905 |

(Continued)

FOREIGN PATENT DOCUMENTS

| | | |
|---|---|---|
| CH | 702396 A2 | 6/2011 |
| DE | 202005019 U1 | 5/2007 |

(Continued)

*Primary Examiner* — Terrell Matthews
(74) *Attorney, Agent, or Firm* — Notaro, Michalos & Zaccaria, P.C.

(57) ABSTRACT

A method and a device for transporting and examining fast-moving objects to be treated, the objects comprising an outer surface and a top surface, (e.g. preforms, bottles, containers, lids, closures). The device comprises an examining unit with an inspection camera and a rejection unit, the bodies being rejected by expulsion using a contactless exertion of force.

12 Claims, 2 Drawing Sheets

(56) References Cited

U.S. PATENT DOCUMENTS

Figure 1:
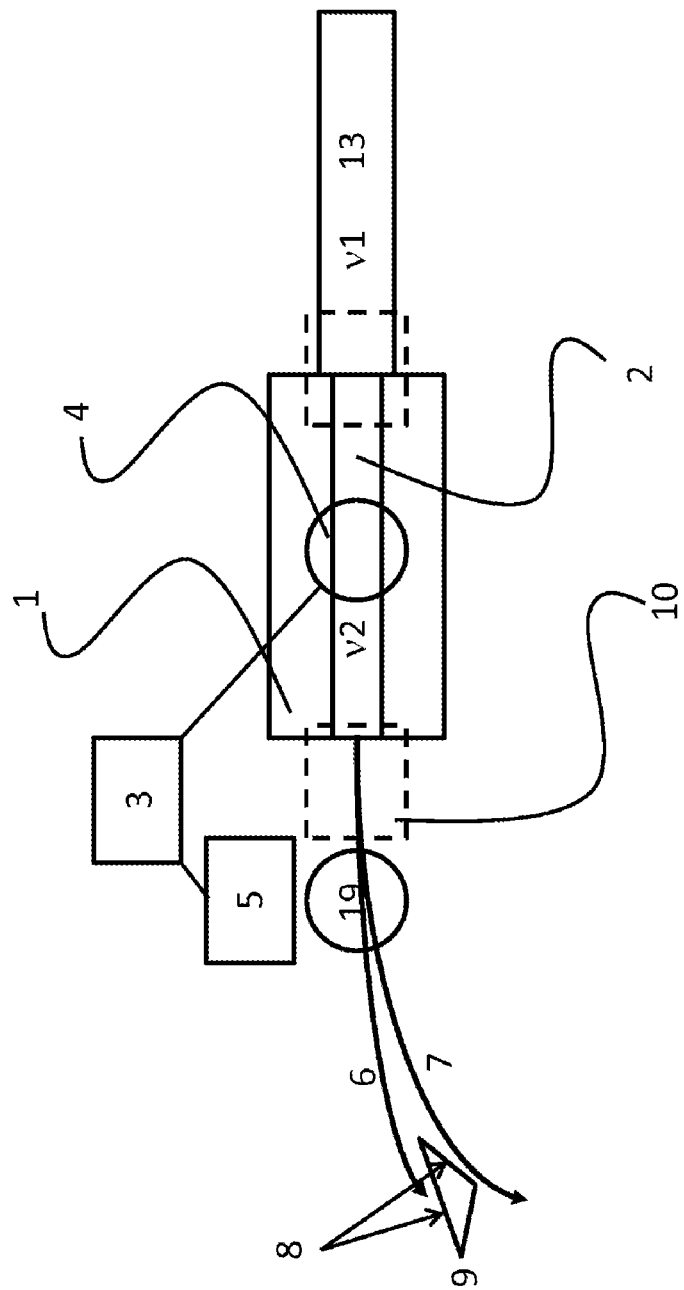

| | | | |
|---|---|---|---|
| 5,659,624 A * | 8/1997 | Fazzari | G06K 9/6253 |
| | | | 209/580 |
| 5,887,073 A * | 3/1999 | Fazzari | G06K 9/6253 |
| | | | 209/580 |
| 5,954,206 A * | 9/1999 | Mallon | B07C 5/342 |
| | | | 209/580 |
| 6,012,344 A | 1/2000 | Halbo | |
| 6,013,887 A * | 1/2000 | Satake | B07C 5/3425 |
| | | | 209/580 |
| 6,060,677 A * | 5/2000 | Ulrichsen | B07C 5/342 |
| | | | 209/577 |
| 6,497,324 B1 | 12/2002 | Doak et al. | |
| 6,646,218 B1 * | 11/2003 | Campbell | A24B 1/04 |
| | | | 209/577 |
| 6,914,678 B1 | 7/2005 | Ulrichsen et al. | |
| 7,262,380 B1 * | 8/2007 | Ulrichsen | B07C 5/342 |
| | | | 209/577 |
| 7,851,722 B2 * | 12/2010 | Ito | B07C 5/3425 |
| | | | 209/576 |
| 8,689,682 B2 * | 4/2014 | Rose | A22C 17/04 |
| | | | 100/121 |
| 8,692,148 B1 * | 4/2014 | Sommer, Jr. | B07C 5/126 |
| | | | 209/576 |
| 2010/0193332 A1 | 8/2010 | Beyerer et al. | |
| 2012/0055855 A1 * | 3/2012 | Ackley, Jr. | B23K 26/0838 |
| | | | 209/580 |
| 2016/0001328 A1 * | 1/2016 | Hermle | B07C 5/363 |
| | | | 209/577 |

FOREIGN PATENT DOCUMENTS

| | | | |
|---|---|---|---|
| EP | 2453225 A2 | 5/2012 | |
| JP | 8-304305 A | 11/1996 | |

* cited by examiner

DEVICE AND METHOD FOR TRANSPORTING AND EXAMINING FAST-MOVING OBJECTS TO BE TREATED

The present invention relates to a device and to a method for transporting and examining fast-moving individual bodies of packaging constituents and packaging precursor products with at least one outer surface and at least one top surface.

Such individual bodies of packagings or packaging constituents or packaging precursor products are for example preforms for blow-molding processes, PET bottles, yoghurt cups, containers, covers, closures, screw caps or generally cylindrical hollow bodies that are closed at one side, which are often constructed as multi-layer plastics bodies. Said bodies thus have at least one outer surface and one top surface, wherein the top surface may comprise an opening. Said bodies may likewise have a base surface which is predominantly parallel to the top surface, if said base surface is not formed by the outer surface in the manner of a cone or rounded cone, such as is the case for example in preforms.

In many technical applications, said bodies must be manipulated and examined with regard to quality. Specifically in the food industry, it is necessary, for reasons of economy, for large quantities to be packaged in the shortest possible time, wherein only mechanically and visually non-defective packagings or packaging constituents must be used. These must firstly be produced then separated and subsequently inspected for defects, which is followed by a rejection of those packagings which are detected as being defective, before the packagings thus examined are transferred to the packaging machine for the packaging process. Here, at least 1,500 individual bodies of the items for handling must be dealt with per minute, such that the time available for each body to be transported, examined and rejected is less than 40 ms. In the case of even higher unit quantities, correspondingly less time is available per body. The separation, inspection and rejection process therefore constitutes a significant constriction in the packaging process, and must be performed correspondingly quickly and reliably.

A separation process for such packagings or packaging constituents is known from CH 702 396 A2, and an examination device for already-separated objects is known from EP 2 453 225 A2. Finally, DE 20 2005 019 111 U1 has disclosed a belt for a handling machine in which it is intended for bottles to be transported and rotated during the transportation process with their base exposed.

US 2010/0193332 A1 has disclosed an examination and rejection device in which non-separated items are ejected in a free throw from a transport belt and fly through the field of view of a color camera. The material flying in the width direction of the transport belt is spanned by a compressed-air nozzle bridge, the nozzles of which are individually actuable such that items detected as being defective can be blown out. "Items" refers in particular to lightweight items or items of low density, such as for example tobacco papers, spices and rice.

Against this background of the prior art, the present invention addresses the method object of proposing a particularly rapid and reliable inspection and rejection step and addresses the device object of proposing a corresponding device.

The method object is achieved by means of a method for transporting and for examining fast-moving bodies of packaging constituents and packaging precursor products with at least one outer surface and at least one top surface, in which method bodies of the items for handling which are transported to an examination unit are received by said examination unit in a conveying path, the conveying path carries the bodies past at least one inspection camera which is connected to a control unit, the control unit, on the basis of the image data originating from the inspection camera, detects the level of defectiveness of each body, and the examination unit transfers the bodies to a rejection unit, wherein either the examination unit or the rejection unit ejects the bodies, in particular approximately in a free throw, and wherein the rejection unit changes the flight paths of bodies detected as being defective and of bodies detected as being non-defective relative to one another by means of a contactless exertion of force. This method highly advantageously permits a very rapid overall process of transport, inspection and rejection, in particular by ejection in a throw, in particular in an approximately free throw. Ejection in a throw advantageously eliminates the need for slide parts, guide members or the like, is structurally simple and also involves little wear owing to the lack of movable parts. The orientation of the flight path in space is, according to the invention, variable within very wide limits; according to the invention, the throw angle may be approximately zero, that is to say the throw path may point approximately vertically downward, said throw angle may be 45°, that is to say the throw path may point obliquely downward, the throw angle may be 90°, that is to say the throw path may be approximately level, or else the throw angle may encompass obtuse angles, that is to say the throw path points obliquely upward or even steeply upward. Through the selection of the suitable flight path, different throw ranges and times of flight and thus also different possibilities for flight path variation are made possible. What are most preferable are approximately horizontal or slightly downwardly directed throws. Likewise preferable are contactless exertions of force, for example by means of a burst of compressed air, as this permits operation without additional mechanical contact with the individual ejected bodies, and also does not damage said bodies. As the bodies of the items for handling have the same geometric shapes, the same mass and the same speed, their respective flight path is also the same, that is to say fluctuates only within very narrow parameters. Owing to this practically identical flight path, precise mechanical guidance for the rejection process is not necessary. The time period available to the control unit for each moving body of the items for handling is the time period between the image capture and entry into the area of action of the rejection unit. Since, in free flight, no forces other than gravitational force act on the items, an exertion of force on the items in the direction of the force of gravity is particularly effective in order to change the respective flight path. According to the invention, the action of force may however also be implemented at any other angle with respect to the force of gravity, specifically also laterally with respect thereto or oppositely thereto, that is to say so as to lengthen the flight path. In addition to the contactless means already mentioned above, the invention also encompasses, by the expression "contactless", all measures which operate without direct mechanical contact between the rejection unit and items for handling, that is to say for example the action of electrical or magnetic fields or pressure waves. By the expression "inspection camera", the invention refers primarily to any type of optical (daylight) camera but also IR cameras or other fast-operating image capture systems. By the expression "inspection camera", the invention furthermore encompasses any other sensor which detects relevant characteristics of the body, such as for example color sensors, which detect the presence of a color and the parameters thereof, that is to say also sensors which can detect, for example, the dimensional conformance of the bodies. Said sensors may for example be measurement sensors, strain gauges, contact sensors or the like which, in the event of non-conformance with the demanded dimensions, transmit a corresponding signal to the control unit, which need not imperatively be an image but may even be a purely yes/no signal. In certain applications, the use of an IR camera, in particular a cooled IR camera, is highly advantageous, as this permits the capture of physically accurate images in extremely rapid succession, such that processing rates of more than 2,500 bodies per minute can be attained. In this case, the cooled IR camera requires less than 0.5 ms to capture an image, that is to say does not constitute a processing constriction, and makes it possible, in visible light, to inspect non-visible structures of the body. Examples of these are EVOH coatings or the like. Here, the invention uses at least one inspection camera, but it is also common for four or more inspection cameras to be used if the geometric structure of the bodies can be adequately detected only using a multiplicity of cameras. In this case, the inspection cameras should be directed toward that section of the body which is respectively to be observed, that is to say should be arranged so as to point laterally, obliquely or vertically; the sequence of viewing directions during the transportation of the bodies may be freely selected, and inspection of a base does not imperatively have to be performed before a lateral inspection, or does not imperatively have to be provided at all.

According to the invention, the rejection unit acts directly at the end of the conveying path or at a distance from the end of the conveying path. If the rejection unit acts, according to the invention, directly adjacent to the examination unit, the flight path is particularly short, as immediate influencing of the flight path is realized. Owing to the resulting very short structure of the rejection unit, no basically idle time is required for the items for handling to be transported further to the rejection unit; rather, the rejection is performed directly after said items pass through the examination unit. Otherwise, the examination unit itself ejects the examined items in a throw, the flight path of which leads through the area of action of the rejection unit. Said rejection unit in turn then changes the flight path of the free-flying bodies as discussed. The spatial separation of the examination and rejection units advantageously makes it possible for further inspection cameras or devices to be interposed, which examine hitherto unexamined regions of the bodies without obstruction by any holding or guide elements. This represents an effective addition to the examination means that have already been used in the region of the examination unit. In free flight, the body surface is accessible, and thus examinable, without obstruction.

As described, the method according to the invention provides that the rejection unit exerts a force on the bodies by means of a contactless exertion of force. Out of the stated ways of contactlessly exerting force, a burst of compressed air is particularly preferred. Owing to the short time available per body of the items for handling, this is ideal, as it is merely necessary for a valve to be opened and closed for this purpose. It is highly advantageous that the use of moving parts, which would have to be returned to their initial position in a time-consuming manner, is avoided. Also, mechanical influencing of the flight path by way of impact or guide edges is advantageously avoided, and no abrasion, jamming or the like can occur. Finally, compressed air is normally easily available at any location at which the device is installed, or at any location at which the method is implemented. Owing to the reaction time in the range of a few milliseconds, however, not all compressed-air valves are suitable; they must have correspondingly short opening and closing times, and also, an adequately high starting pressure must be provided. Finally, the air flow impinging on the items for handling must not have been intensely diffused and must not have covered an unduly great distance, such that it impinges with impulse action at an accurate position and influences only the respectively desired item for handling. This is particularly important as, by contrast to devices for non-separated bulk items such as grains of rice, tobacco papers or the like, physically accurate rejection is necessary in order to keep the reject rate as low as possible and in particular in order that the much larger bodies in the case of the method and device according to the invention can be impinged on with a force adequate to change the flight path. A valve that can be used must therefore have such characteristics.

According to the invention, the conveying path carries the bodies, with a base and/or top exposed, past the at least one inspection camera, such that said inspection camera can examine the base, the top surface or the base and top surface. This is realized in particular by way of a frictionally engaging parallel belt pass, as will be discussed further below.

It is also provided according to the invention that the conveying path of the examination unit rotates the bodies about their longitudinal axis as they pass through the examination unit, for example by way of two belts running at different speeds. In this way, it is highly advantageously made possible for the entire circumference of the body to be examined in the examination unit, for example by virtue of three or more images being captured along the delivery path by way of a corresponding number of cameras.

In a refinement of the method, it is provided that at least one inspection camera images a base surface of the bodies and at least one inspection camera images a side surface of the bodies, and in particular, the bodies which are in free flight are, before the rejection stage, subjected to lateral inspection by way of up to four or more inspection cameras pointing at the side thereof, wherein all of the inspection cameras are connected to the control and evaluation unit. The method thus makes it possible to inspect the entire surface of the bodies for handling, in particular also through the use of more than two sensors/inspection cameras. According to the invention, the inspection may be performed both by fast daylight cameras and by very fast-operating cooled IR cameras, which have exposure times of a few hundred microseconds and which image each individual body of the items for handling in an exact and positionally accurate manner. Said cooled IR cameras are provided according to the invention in particular if the bodies must be inspected with regard to the quality of a barrier coating which cannot be seen in visible light. Here, in the case of the invention, it is not of importance whether firstly a base-side or top-side inspection and subsequently a lateral inspection of the bodies is performed or vice versa. It also falls within the invention for the base side and top side to be imaged in free flight by means of the sensors after the sides have already been imaged. It likewise falls within the invention for no further sensors to be used in the free flight situation, but for the surface inspection to have been performed already in the examination unit, by means of cameras arranged there in top-facing, base-facing and/or side-facing positions, before the rejection step.

In a refinement of the method, it is also provided that at least one flight path leads past a separating surface of a separating body, and in particular, each flight path leads past a respective separating surface, wherein the two separating surfaces, between them, enclose an angle. The reliability of the rejection process is advantageously further increased by means of this contactless separating device, as the flight path separation that has already been initiated cannot be reversed, for example by unintended turbulence or bursts of air. The bodies, once separated, remain on their flight paths which are separated from one another by separating surfaces.

Finally, in a refinement of the method, it is also provided that only those bodies of the items for handling which are determined as being non-defective are subjected to a change in their flight path. This increases the reliability of the rejection process, as in the event of a fault at the rejection unit, all items for handling are separated out, and thus it is not possible for an item for handling which has been detected as being damaged or defective to erroneously become mixed up with items for handling that have been evaluated as being non-defective.

It is likewise provided according to the invention that the bodies in free flight are, before the rejection stage, subjected to lateral inspection by way of inspection cameras pointing at the side thereof, wherein said sensors are likewise connected to the control and evaluation unit. The rejection is then performed at a later stage in the free flight. In this way, it is advantageously possible to document the entire body surface, and to thus attain a very high level of quality control. Finally, in the case of particular items for handling, inspection of the top side and/or bottom side is also important, in particular in the case of caps, as the face surface thus observed is at the same time the most relevant surface of the body, as has already been discussed.

Finally, the method according to the invention also encompasses a second rejection which follows the first rejection. This highly advantageous refinement permits additional security against erroneous method implementation. If the first rejection step is unsuccessful, for example because the camera, the data transmission, the data processing, the compressed-air control or the like are not functioning correctly, said second rejection step prevents erroneous approval of non-examined or defective but unrejected bodies. According to the invention, said second rejection step blocks the flight path of all bodies and thus prevents even only one defective packaging part from being allowed through. The blocking may be effected contactlessly, in particular by way of bursts of compressed air, or may be effected by way of contact, for example by the movement of an arm, of a barrier or generally of a physical body into the flight path(s) of the bodies. It is also possible according to the invention for only those bodies which have been detected as being defective but which have not been rejected in the first rejection step to be rejected.

The device object is achieved by means of a device for transporting and examining fast-moving individual bodies of packaging constituents and packaging precursor products with at least one outer surface and at least one top surface, having a) an examination unit, wherein the examination unit has at least one inspection camera, a control unit connected to said inspection camera, and a transport device, wherein the transport device transports the bodies of the items for handling past the at least one inspection camera, wherein the control unit determines the level of defectiveness of each body on the basis of the image data originating from the at least one inspection camera, and b) furthermore having a rejection unit which is designed to be functionally connected to the examination unit, wherein the rejection unit receives the bodies originating from the examination unit, wherein either the examination unit or the rejection unit ejects the bodies in a free throw, wherein the rejection unit influences the flight paths of bodies detected as being defective and of bodies detected as being non-defective relative to one another by means of a contactless exertion of force. The advantages of said device have already been discussed in the discussion of the method according to the invention.

In a refinement of the device, it is provided that the transport device transports the bodies, with a base and/or top exposed, past at least one inspection camera of the examination unit.

According to the invention, the transport device may also at least partially be formed as an overhead guide, that is to say hold the bodies at the top surface thereof, for example by being configured as a vacuum belt. In any case, the transport device must carry the bodies smoothly past the camera, that is to say oscillating movements or oblique positions must imperatively be avoided. If said transport device is in the form of an overhead guide before the camera, it is provided according to the invention that said transport device is designed to end in a wedge-shaped or dovetail-shaped manner at the camera-side end thereof. The stated shapes apply in each case in a top view or view from below. It is achieved in this way that the bodies are expediently made contact with last at an edge layer, that is to say radially far to the outside; in the latter case, the contact is even symmetrical. In this way, for the capturing of an image of the upper side of the body or of the underside thereof, unfavorable oblique positions or movements are eliminated, which is particularly important in particular in the case of preforms. If use is to be made only of lateral cameras, the entire transport device may be in the form of an overhead guide. In this case, the stated end shape should be provided in the region of the transfer to the rejection unit, so as to always ensure identical flight attitudes of the bodies.

In a refinement of the device, it is provided that the transport device has two belts which run around in each case one drive wheel and one further wheel and which are driven and pretensioned and which, between them, define a conveying path. Such a belt-type transport arrangement permits gentle, damage-free guidance of the bodies with a clamping force adequate to ensure that the bodies are guided in a rotationally fixed manner and clear image capturing is made possible. The spacing between the two belts in the conveying path is therefore slightly smaller than the free outer diameter of the bodies. By means of revolving belts, it is possible in a structurally simple manner to realize high transportation speeds, for example of 5 m/s. The belt-type transport arrangement provided according to the invention furthermore has the advantage of easily dealing with fluctuations in the supply of bodies; a particular spacing of the bodies relative to one another, as in the case of rotary plate-based or nested transportation, is not required.

In a refinement of the invention, it is provided that the belts of the transport device revolve at mutually different speeds. The advantages of this refinement have already been discussed further above.

It is also provided according to the invention that at least one belt, preferably both belts, is/are in the form of a toothed belt, and/or one wheel is provided as guide wheel and/or one wheel is provided as second drive wheel, and/or at least one idler wheel is provided for each belt. At the required high transportation speeds belts driven permanently by purely frictionally engaging action are not without problems, as the surface thereof can become glazed through possible slippage, such that toothed belts with drive gearwheels may be more advantageous. According to the invention, however, the use of smooth belt surfaces is in no way ruled out.

According to the invention, one drive wheel and one guide wheel, or two drive wheels, may be provided per belt. Between these, one or more idler wheels may be arranged so as to generate a certain pretension in the belt and prevent vibration thereof. Alternatively or in addition, the belts may be pretensioned by means of a spring force, for example by virtue of the idler wheels being arranged so as to be radially displaceable counter to a spring force.

In a refinement of the invention, it is provided that the rejection unit has a compressed-air valve, in particular a compressed-air valve with closing and opening times of less than 3.5 ms. The advantages of this refinement have been described above.

Finally, it is also provided that the device has a separating body for separating flight paths, said separating body having at least one separating surface, in particular having two separating surfaces which, between them, enclose an angle. Said separating body prevents the non-defective and defective items for handling, which have already been separated in terms of their flight paths, from becoming mixed up again as a result of unintended disturbances.

If a second rejection unit which follows the first rejection unit as viewed in the flight path of the bodies is provided, the operational reliability of the device is advantageously increased, as mentioned above. If the first rejection unit or even the examination unit as a whole should fail, the second rejection unit blocks the flight path of the bodies entirely, thus preventing the device from approving defective bodies. The device as a whole then enters a fault mode and must be actively re-enabled by an operator after the malfunction has been eliminated. It therefore likewise falls within the invention for a sub-unit to be provided for the first rejection unit, which sub-unit checks whether the rejection of a body has actually taken place. This may be realized for example by way of a light barrier that must be passed through by a rejected body, a pressure-sensitive panel which is struck by the body, or the like. Thus, if a body detected as being defective does not pass through said light barrier, for example, the first rejection has failed, and the described second rejection unit is activated. Alternatively, according to the invention, provision is also made for the flight path of the non-defective bodies to be monitored. This means that the second rejection stage is activated if a body that should in fact have previously been rejected flies through the light barrier. The second rejection unit is also activated for example if the camera does not output any images, or some other fault occurs upstream of the second rejection unit and said fault is signaled to said second rejection unit. It also falls within the invention for the second rejection unit to operate merely as a backup for the first rejection unit and, if the fault detection by camera and controller is operating correctly but it is merely the case that the defective body has not been rejected in the first rejection unit, for said second rejection unit to reject said body, for example again by a burst of compressed air or by mechanical contact.

Finally, it is also provided according to the invention that the examination unit has a second conveying path in which the bodies are guided at the base side and/or top side, wherein said conveying path leads past at least one inspection camera which points toward the bodies. Said second delivery path may directly adjoin the first delivery path or may be arranged upstream of said first delivery path in terms of the process. In both cases, a transfer region between the two delivery paths must be provided. With regard to the invention, it is important that inspection of the bodies can also be performed already upstream of the examination unit itself, in particular if this yields a shorter structural length of the device or is necessary owing to a longer processing time period necessitated by the bodies.

The abovementioned features highly advantageously yield, with little outlay in terms of construction, a device which operates quickly and reliably.

Figure 2:
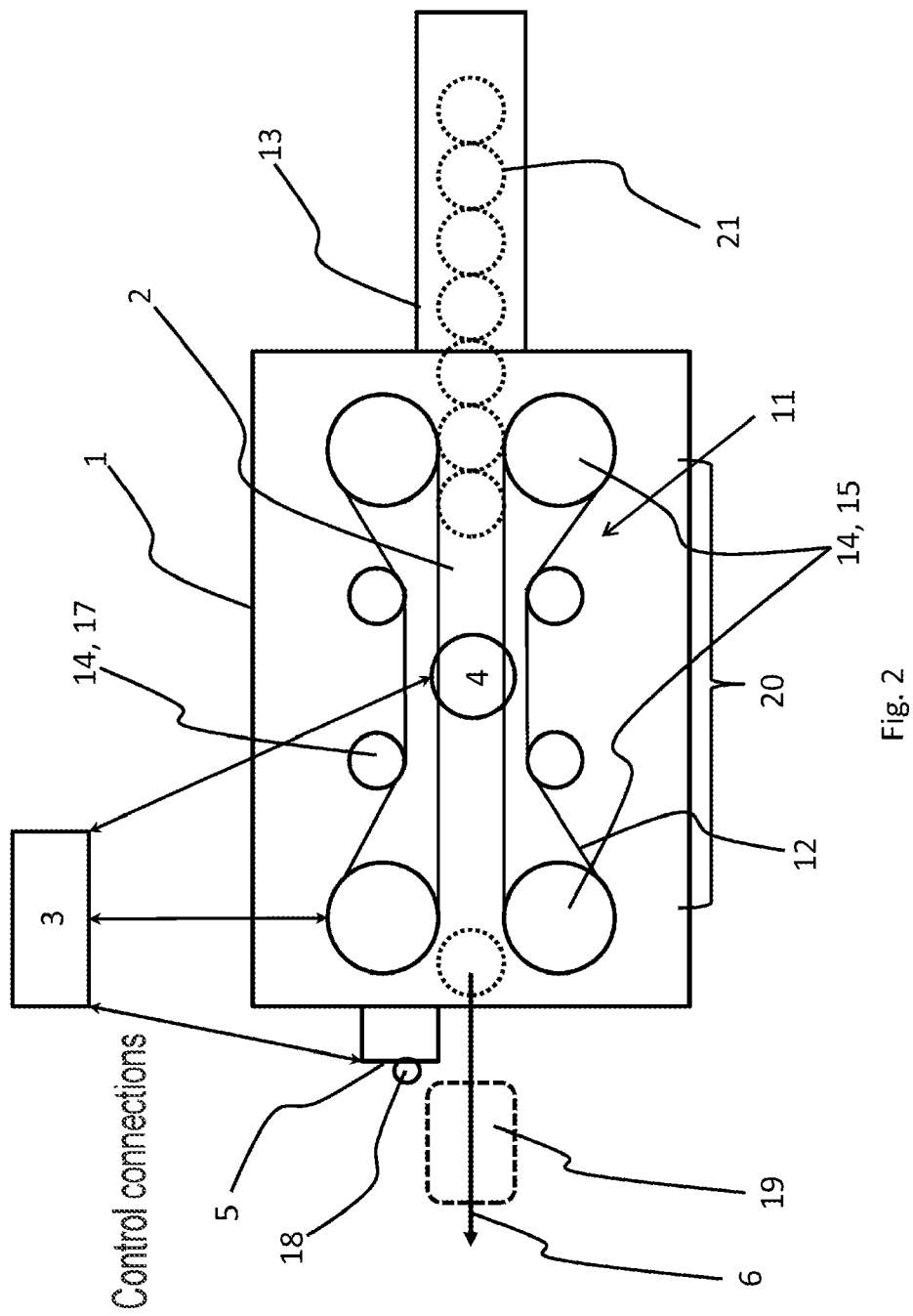

Further details, advantageous refinements and a preferred embodiment will be discussed in more detail below on the basis of the description of the figures, in which:

FIG. 1 shows a diagrammatic side view of a device according to the invention, and FIG. 2 shows a view from below of an examination unit according to the invention.

FIG. 1 shows a diagrammatic side view of an embodiment according to the invention. Illustrated on the right-hand side is a feed device 13 which transfers the items for handling from a first separation device (not illustrated) and transfers said items as a continuous stream of bodies 21, which are in contact with one another, to the examination unit 1 and, in so doing, finally separates said bodies such that the bodies 21 are no longer in contact. Said feed device 13 transports the bodies 21 at a first speed, with said bodies either standing on a belt or being suspended from a vacuum-type belt. For the final separation, a second, accelerating transport section may be provided which accelerates the bodies to a second speed, specifically the speed prevailing in the examination unit 1. In this case, the bodies are, as discussed, packagings or packaging precursor products such as preforms, caps, cups or the like. The examination unit 1 has an inspection camera 4 which, in this example, is in the form of a daylight camera or cooled IR camera. Other imaging sensors and other sensors likewise fall within the invention, as described above. The inspection camera 4 points from above or below toward the face side of the bodies 21 of the items for handling, and is connected operatively and for data transmission to a control unit 3. Said control unit 3 receives data from the camera 4, specifically images of individual bodies 21 of the items for handling, and compares said images with target values. Depending on the items for handling, the inspection camera 4 is a daylight camera or an, in particular cooled, IR camera. With the latter, it is possible to determine the presence, the completeness and the thickness of an (EVOH) barrier coating on each body. Depending on the items for handling, the control unit may also determine the presence and the quality of other layers in the wall material of the bodies. The bodies are transported through the examination unit 1 along a conveying path 2 which leads past under/over the view axis of the camera 4. According to the invention, said conveying path may have two belts 12 running at different speeds, such that the body 21 guided between them performs a rotation about the longitudinal axis thereof as it passes through the examination unit. In this way, it is possible for laterally pointing cameras provided according to the invention to image and inspect the full circumference of a body. This is the case if the side surface is not concealed by the belts. At the end of the examination unit 1, a rejection unit 5 is arranged such that it can act on bodies 21 that have exited the examination unit 1. In the simplest case, the rejection unit 5 is provided directly downstream of the end of the conveying path 2 of the examination unit 1, which, in this example, ejects the examined bodies 21 approximately in a level throw. The rejection unit 5 is designed to be connected to the control unit 3 and has a valve 18, in particular a nozzle which can be closed by means of a valve and the nozzle opening of which is directed toward the flight path of the bodies 21. If the control unit 3, on the basis of the data from the one or more cameras 4, detects that a body 21 is defective, said control unit sends a control signal to the valve 18 or the nozzle and opens the latter at a time selected such that a burst of compressed air emerging from the nozzle acts on the body when it enters the area of action 19 of the nozzle of the rejection unit 5. Thus, on the basis of the distance between the area of action 19 and camera 4, the distance between the nozzle opening and area of action 19, the opening and closing times of the valve, the transportation speed of the body and the time of flight thereof until it reaches the area of action 19, the control unit calculates the time at which the valve must be opened in order that the burst of pressure can influence the flight path of the body 21. The flight path 6 of the defective bodies subsequently differs from the flight path 7 of the non-defective bodies such that reliable separation of the bodies is ensured. To increase reliability, there is arranged between the flight paths 6, 7 a separating body 9, which in this case has two separating surfaces 8.

Dashed lines in FIG. 1 show two, thus optional, positions for one or more additional cameras 10 which image the side or outer surfaces of the body without disruption when said bodies are in free flight. Said two positions are situated downstream or upstream of the position of the first camera 4. In the former case, the lateral camera(s) 10 may be arranged so as to observe the bodies in flight, and may thus be arranged between the area of action 19 of the rejection unit 5 and the end of the conveying path 2 of the examination unit 1. In the latter case, the lateral camera(s) 10 are arranged so as to operate in the region between the start of the conveying path 2 and the end of the feed path of the feed device 13. The illustration does not show a second rejection unit, which may also be provided according to the invention, downstream of the first rejection unit 5. As discussed above, said second rejection unit would either serve as a backup for the first rejection unit or, by blocking the flight path(s) of the bodies, reject all of the bodies and thus shut down the operation of the device as a whole. Said second rejection unit is preferably arranged in the flight path which is normally not influenced by the first rejection unit, as the blocking of said flight path in the event of malfunctions is important because said flight path also includes defective bodies. The second rejection unit also comprises a corresponding controller and a detection device for detecting the effectiveness and functioning of the first rejection unit or of the entirety of the device upstream. According to the invention, said detection device may monitor the flight paths both of the rejected bodies and of the non-defective bodies, as described.

FIG. 2 shows an examination unit 1 according to the invention in a view from below. It is possible to clearly see the camera 4 which is arranged within a conveying path 2 and which points from above toward the bodies of the items for handling that are transported past said camera. A feed device 13 introduces pre-separated and finally separated bodies into the area of action of the conveying path 2 and, if appropriate, accelerates said bodies to the transportation speed $v_2$ prevailing in the conveying path 2. According to the invention, the transportation is realized by way of two belts 12 which each revolve in endless fashion about two drive wheels 15. In this example, no guide wheel is provided; otherwise, one of the two drive wheels 15 of a belt 12 would be configured as a guide wheel of said type. For each belt 12, it is also the case that two idler wheels 17 are provided which tension the respectively associated belt 12 such that the latter does not vibrate despite the high belt speeds of 5 m/s. The delivery path 2 itself is formed by a section 20 in which the two belts, facing toward one another, run approximately parallel. Belts 12 that may be used have a soft but rough surface which is suitable for making contact with the items for handling in a forceful but gentle manner. The width between the belts 12 in the section 20 may in this case be set to be slightly smaller than the outer diameter of the items for handling. The belts 12 may be toothed belts and may be of multi-layer construction, and may revolve at mutually different speeds. In the illustrated example, the examination unit 1 itself is designed to eject the bodies in a free horizontal throw. A rejection unit 5 is arranged such that it can influence the flight path for specific bodies so as to change said flight path in a manner dependent on defects.

With this invention, it is by all means possible for 4,500 bodies per minute to be handled and inspected, though a throughput of more than 5,000 bodies per minute through the device is also possible. The combination of prior complete separation, fast-running belts 12, very fast image capture by way of a daylight or cooled IR camera and contactless rejection, by way of a change in flight path, of the bodies that have been monitored and detected as being defective is particularly suitable for dealing with items for handling that are moving at such high speeds.

LIST OF REFERENCE NUMERALS

1 Examination unit
2 Conveying path
3 Control unit
4 Inspection camera
5 Rejection unit
6 Flight path
7 Flight path
8 Separating surface
9 Separating body
10 Lateral inspection camera
11 Transport device
12 Belt
13 Feed device
14 Wheel
15 Drive wheel
16
17 Idler wheel
18 Compressed-air valve
19 Area of action
20 Parallel belt section
21 Body

The invention claimed is:

1. A device for transporting and examining fast-moving individual bodies (21) of packaging constituents and packaging precursor products with at least one outer surface and at least one top surface, comprising:
an examination unit (1), wherein the examination unit (1) has at least one inspection camera (4), a control unit (3) connected to said inspection camera, and a transport device (11), wherein the transport device (11) transports the bodies (21) by means of two driven and pretensioned belts (12) which each run around one drive wheel (15) and one further wheel (14) with a base and/or top exposed past the at least one inspection camera (4), whereby the transport device (11) is at least formed as an overhead guide, to hold the bodies (21) at the top surface thereof ending in a wedge-shaped or dove-tail shaped manner contacting the bodies at an edge layer, radially far to the outside to carry the bodies (21) smoothly past the camera (4) to avoid oscillating movements or oblique positions wherein the control unit (3) determines the level of defectiveness of each body (21) on the basis of the image data originating from the at least one inspection camera (4), and furthermore having a rejection unit (5) which is designed to be functionally connected to the examination unit (1), wherein the rejection unit (5) receives the bodies (21) originating from the examination unit (1), wherein either the examination unit (1) or the rejection unit (5) ejects the bodies (21) in a free throw, wherein the rejection unit (5) influences the flight paths (6, 7) of bodies (21) detected as being defective and of bodies (21) detected as being non-defective relative to one another by means of a contactless exertion of force, whereby the bodies (21) in free flight are subjected to lateral inspection before the rejection stage by way of inspection cameras (10) pointing at the side thereof, wherein all of the inspection cameras (4, 10) are connected to the control and evaluation unit.

2. The device as claimed in claim 1, characterized in that the transport device (11) transports the bodies (21), with a base and/or top exposed, past at least one inspection camera (4) of the examination unit (1).

3. The device as claimed in claim 1, characterized in that the transport device (11) has two belts (12) which run around in each case one drive wheel (15) and one further wheel (14) and which are driven and pretensioned and which, between them, define a conveying path (2).

4. The device as claimed in claim 1, characterized in that the belts (12) of the transport device (11) revolve at mutually different speeds.

5. The device as claimed in claim 4, characterized in that at least one belt (12), preferably both belts (12), is/are in the form of a toothed belt, and/or one wheel (14) is provided as guide wheel and/or one wheel (14) is provided as second drive wheel (15), and/or at least one idler wheel (17) is provided for each belt (12).

6. The device as claimed in claim 1, characterized in that the rejection unit (5) has a compressed-air valve (18), in particular a compressed-air valve with closing and opening times of less than 3.5 ms.

7. The device as claimed in claim 1, characterized in that the at least one inspection camera (4, 10) is selected from daylight cameras, IR cameras, cooled IR cameras, color sensors, sensors for determining conformance of one or more outer dimensions of a body (21), or from several of these.

8. The device as claimed in claim 1, characterized in that said device has a separating body (9) for separating flight paths (6, 7), said separating body having at least one separating surface (8), in particular having two separating surfaces (8, 8') which, between them, enclose an angle.

9. The device as claimed in claim 1, characterized in that a second rejection unit (5) which follows the first rejection unit as viewed in the flight path of the bodies (21) is provided.

10. The device as claimed in claim 1, characterized in that the examination unit has a second conveying path (13) in which the bodies are guided at the base side and/or top side, wherein said conveying path (13) leads past at least one inspection camera (4) which points toward the bodies.

11. The device as claimed in claim 2, characterized in that belts (12) of the transport device (11) revolve at mutually different speeds.

12. The device as claimed in claim 3, characterized in that belts (12) of the transport device (11) revolve at mutually different speeds.

* * * * *